(12) United States Patent
Cummins

(10) Patent No.: US 9,642,893 B2
(45) Date of Patent: May 9, 2017

(54) METHOD FOR REDUCING INJURY AND STABILIZING MUSCLE USING ORALLY ADMINISTERED INTERFERON

(71) Applicant: Joseph Cummins, Edmond, OK (US)

(72) Inventor: Joseph Cummins, Edmond, OK (US)

(*) Notice: Subject to any disclaimer, the term of this patent is extended or adjusted under 35 U.S.C. 154(b) by 0 days.

(21) Appl. No.: 14/324,053

(22) Filed: Jul. 3, 2014

(65) Prior Publication Data

US 2015/0010507 A1    Jan. 8, 2015

Related U.S. Application Data

(60) Provisional application No. 61/842,797, filed on Jul. 3, 2013.

(51) Int. Cl.
| | | |
|---|---|---|
| *A61K 38/21* | (2006.01) | |
| *A61K 8/03* | (2006.01) | |
| *A61K 33/00* | (2006.01) | |
| *A61K 9/00* | (2006.01) | |
| *A61K 47/26* | (2006.01) | |
| *A23K 40/35* | (2016.01) | |
| *A23K 20/147* | (2016.01) | |
| *A23K 20/163* | (2016.01) | |
| *A23K 50/10* | (2016.01) | |
| *A23K 50/60* | (2016.01) | |

(52) U.S. Cl.
CPC .......... *A61K 38/212* (2013.01); *A23K 20/147* (2016.05); *A23K 20/163* (2016.05); *A23K 40/35* (2016.05); *A23K 50/10* (2016.05); *A23K 50/60* (2016.05); *A61K 9/0056* (2013.01); *A61K 38/21* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 4,462,985 A | 7/1984 | Cummins, Jr. | |
| 4,497,795 A | 2/1985 | Cummins | |
| 4,820,514 A | 4/1989 | Cummins | |
| 4,820,515 A | 4/1989 | Cummins | |
| 5,017,371 A | 5/1991 | Cummins | |
| 5,019,382 A | 5/1991 | Cummins, Jr. | |
| 5,215,741 A | 6/1993 | Young et al. | |
| 5,817,307 A | 10/1998 | Cummins | |
| 5,824,300 A | 10/1998 | Cummins | |
| 5,830,456 A | 11/1998 | Cummins | |
| 5,846,526 A * | 12/1998 | Cummins | A61K 38/21 424/464 |
| 5,882,640 A | 3/1999 | Cummins | |
| 5,910,304 A | 6/1999 | Cummins | |
| 6,372,218 B1 | 4/2002 | Cummins | |
| 6,506,377 B2 * | 1/2003 | Cummins | A61K 38/212 424/85.1 |
| 6,656,920 B2 | 12/2003 | Fox et al. | |
| 2006/0242724 A1 * | 10/2006 | Carlton | A01K 67/0275 800/18 |
| 2007/0196416 A1 * | 8/2007 | Li | A61K 9/0019 424/422 |
| 2007/0237723 A1 | 10/2007 | Cummins et al. | |
| 2010/0202982 A1 * | 8/2010 | Yoshioka | A23K 1/1631 424/49 |

OTHER PUBLICATIONS

Baid et al. (2012), J. of Nutrition and Metabolism, vol. 2101, pp. 1-14.*

* cited by examiner

*Primary Examiner* — Christine J Saoud
*Assistant Examiner* — Jegatheesan Seharaseyon
(74) *Attorney, Agent, or Firm* — Shannon L Warren

(57) ABSTRACT

The present disclosure is directed to compositions and methods for treating or preventing muscle injury or diseases through oral administration of low doses of type I and/or type III interferons. In one embodiment a composition is administered comprising interferon-alpha and trehalose.

12 Claims, 7 Drawing Sheets

TABLE

UNWEIGHTED LEASE SQUARES LINEAR REGRESSION OF CK PREDICTOR

| VARIABLES | COEFFICIENT | STD Error | STUDENT'S T | P |
|---|---|---|---|---|
| CONSTANT | 238.92 | 65.5221 | 3.65 | 0.0007 |
| TIME | 4.25949 | 4.48599 | 0.95 | 0.3473 |

R-SQUARED 0.0192
RESID. MEAN SQUARE (mse) 96166.4
ADJUSTED R-SQUARED -0.0021
STANDARD DEVIATION 310.107

| | DF | SS | MS | F | P |
|---|---|---|---|---|---|
| REGRESSION | 1 | 86700.4 | 86700.4 | 0.9 | 0.3473 |
| RESIDUAL | 46 | 4423655 | 96166.4 | | |
| TOTAL | 47 | 4510355.4 | | | |

CASES INCLUDED 48
MISSING CASES 0

COMPARISON OF REGRESSION LINES FOR CK = TIME

| TRT | N | INTERCEPT | SLOPE | MSE |
|---|---|---|---|---|
| A | 12 | 339.821 | 11.6183 | 354126 |
| B | 12 | 250.071 | 1.72768 | 11171.5 |
| C | 12 | 191.607 | 2.02902 | 10338.6 |
| D | 12 | 174.179 | 1.66295 | 2852.52 |

| CHI-SQ | DF | P |
|---|---|---|
| 62.71 | 3 | 0 |

BARTLETT'S TEST OF EQUAL VARIANCES

| COMPARISON | F | DF | P |
|---|---|---|---|
| COMPARISON OF SLOPES | 0.3 | 3, 40 | 0.8222 |
| COMPARISON OF ELEVATIONS | 2.05 | 3, 43 | 0.1217 |

FIG. 1

METHOD FOR REDUCING INJURY AND STABILIZING MUSCLE USING ORALLY ADMINISTERED INTERFERON

CROSS-REFERENCE TO RELATED APPLICATIONS

This application claims the benefit of provisional U.S. Patent Application No. 61/842,797, filed on Jul. 3, 2013.

The applicant is listed as an inventor on all of the applications and patents found in the IDS form and listed here—these are incorporated by reference—U.S. Pat. Nos. 4,462,985; 4,497,795; 4,820,514; 4,820,515; 5,017,371; 5,019,382; 5,215,741; 5,817,307; 5,824,300; 5,830,456; 5,846,526; 5,882,640; 5,910,304; 6,372,218; 6,506,377; 6,656,920; and 20070237723.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

Disclosed herein is an improved system and method for treatment using orally administered interferon. A review of the prior art does not disclosed the current improved system and method. A disclosure of the improved system and method follow in the Detailed Description of the Invention section below.

BRIEF SUMMARY OF THE INVENTION

A system and three methods are disclosed.

Said system comprises a supplemented animal feed. Said supplemented animal feed comprising: a feed supplement comprising a type I interferon, a trehalose, and a disaccharide. Said disaccharide is selected from a group consisting of a maltose, a lactose and a fructose. Said feed supplement is admixed with an animal feed formulation.

Said first method comprises a method of treating muscle injury or disease. Said method comprising: identifying a humans or an animals at risk and administering to said humans or said animals a composition comprising a dose of an interferon.

Said second method comprises a method of stabilizing muscle in a vertebrate species. Said method comprising: administering a composition to a vertebrate species. Wherein, said composition comprises an interferon comprising of an interferon-alpha, an interferon-omega and/or an interferon-lambda.

Said third method comprises a method of inhibiting muscle injury to humans or animals, comprising: administering a composition comprising interferon-alpha, interferon-omega and/or interferon-lambda.

BRIEF DESCRIPTION OF THE SEVERAL VIEWS OF THE DRAWING

FIG. 1 illustrates a data table.

DETAILED DESCRIPTION OF THE INVENTION

Figure 2:
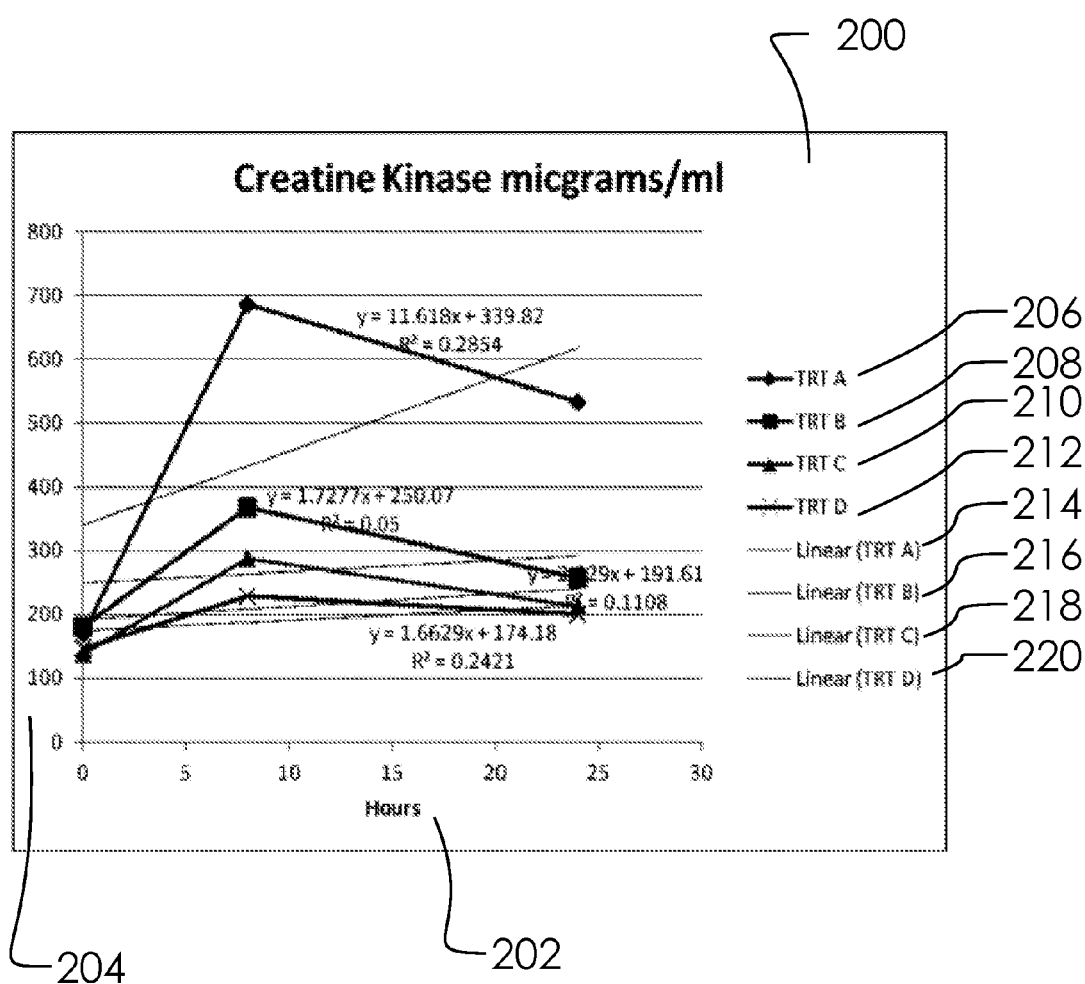
FIG. 2 illustrates a graph.
Figure 3:
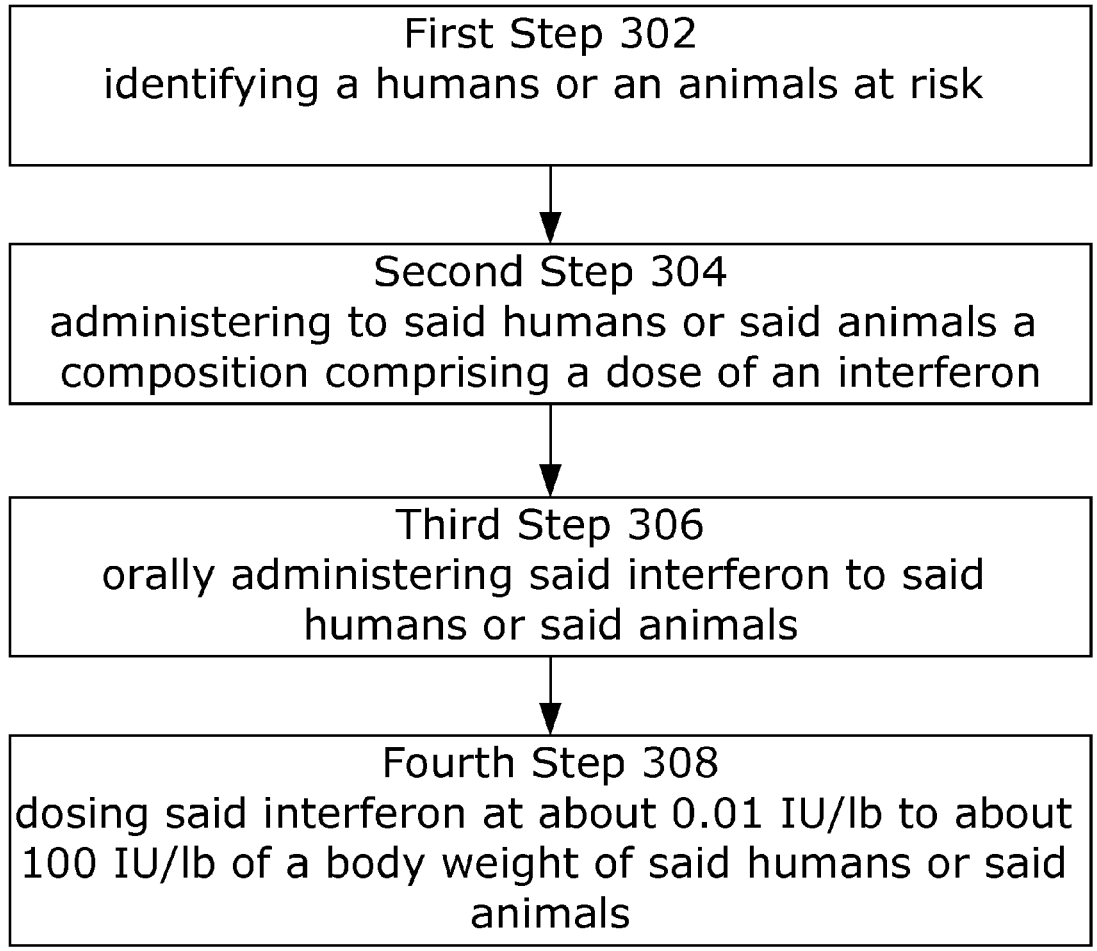
FIG. 3 illustrates a flow chart illustrating a method of treating muscle injury or disease comprising of a first step, a second step, a third step, and a fourth step.
Figure 4:
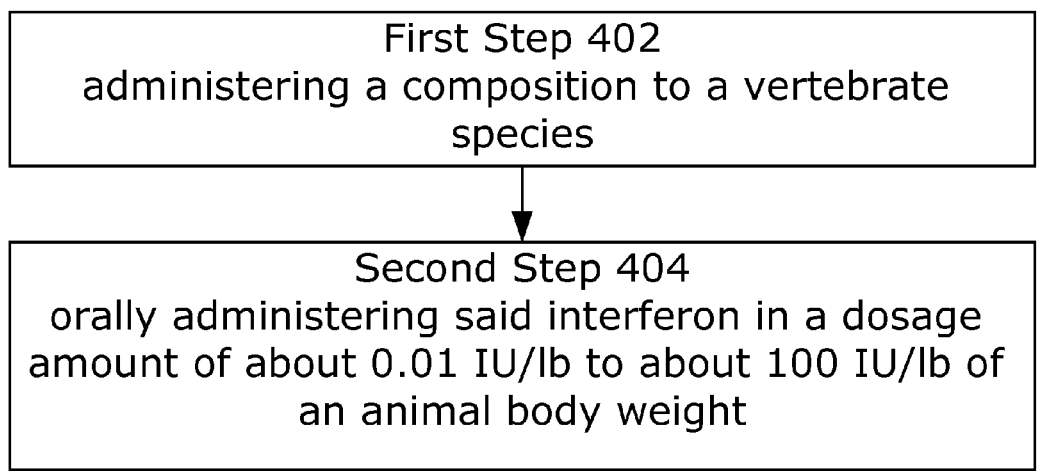
FIG. 4 illustrates a flow chart illustrating a method of stabilizing muscle in a vertebrate species comprising of a first step, and a second step.
Figure 5:
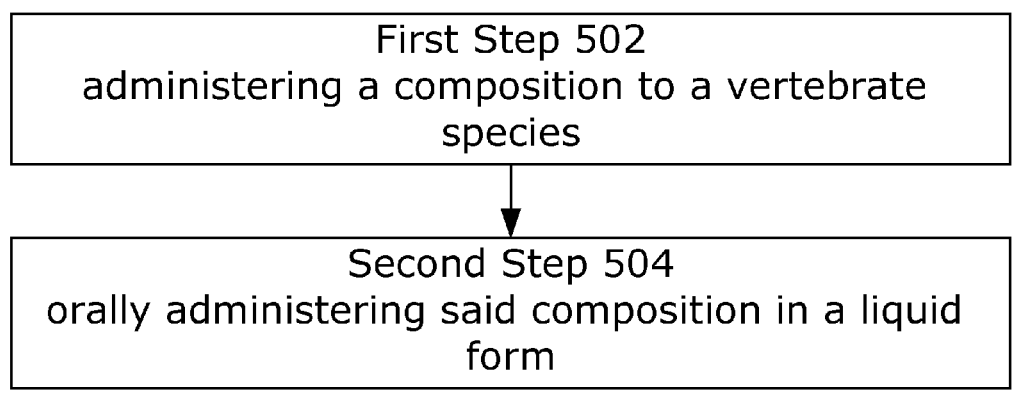
FIG. 5 illustrates a flow chart illustrating a method of stabilizing muscle in a vertebrate species comprising of a first step, and a second step.
Figure 6:
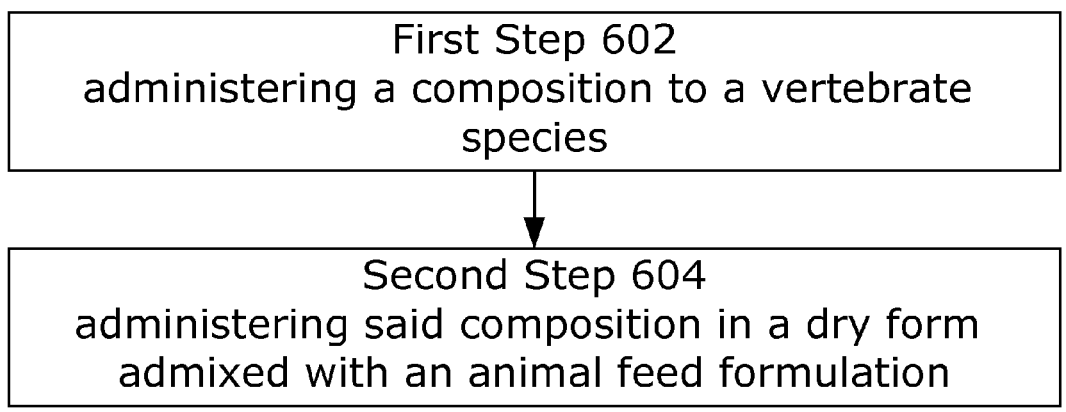
FIG. 6 illustrates a flow chart illustrating a method of stabilizing muscle in a vertebrate species comprising of a first step, and a second step.
Figure 7:
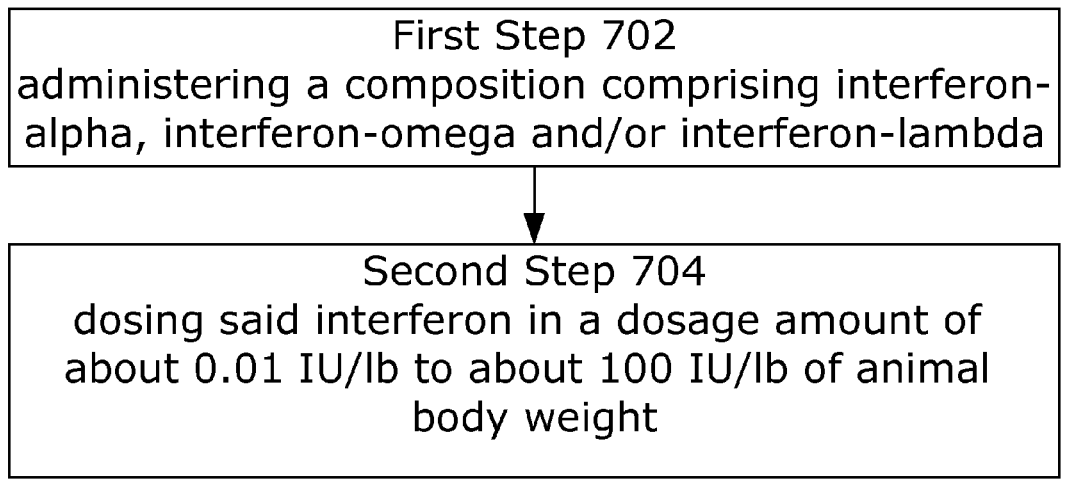
FIG. 7 illustrates a flow chart illustrating method of treating muscle injury or disease comprising of a first step, and a second step.

Described herein is a system and method for treatment of muscle stress, injury or disease using orally administered interferon. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

"Interferon" is a term generically describing a distinct group of cytokines exhibiting pleiotropic activity generally categorized as antiviral, antiproliferative and immunomodulatory. In the early years of interferon (IFN) research, an international committee was assembled to devise a system for orderly nomenclature of the various IFN species and defined "interferon" as follows: To qualify as an interferon, a factor must be a protein which exerts virus non-specific, antiviral activity at least in homologous cells through cellular metabolic process involvinsynthesis of both RNA and protein. "Interferon" as used herein in describing the present disclosure shall be deemed to have that definition and shall contemplate such proteins and glycoproteins, including for example, the subtypes IFN-α, IFN-β, IFN-δ, IFN-γ, IFN-ε, IFN-κ, IFN-λ, IFN-ω and IFN-τ, regardless of their source or method of preparation or isolation. Based on structure, physicochemical properties and biological activities, the IFNs are classified into three major groups: type I, type II or type III. In mammals, seven families of type I IFN have been described. These are: IFN-α, IFN-β, IFN-δ, IFN-ε, IFN-κ, IFN-ω and IFN-τ. Prominent members of the type I IFN and type III IFN that are germaine to this patent application are IFN-α and IFN-ω and the type III IFN-λ. The only type II interferon is IFN-γ and it is not germaine. Among these families, trophoblast IFN-τ, is found only in ruminants and is not virus induced. Rather it is produced in the embryonic trophoblasts during early pregnancy and its production and actions are needed for successful completion of pregnancy. IFN-δ (delta), a polypeptide of about 149 amino acids, has been described only in pigs. Like IFN-τ above, this IFN is produced by trophoblasts and is associated with successful reproduction in swine species.

Creatine kinase isoenzymes (hereafter "CK") are the most organ-specific enzymes in clinical use. Creatine kinases are found in many types of cells, but they have their highest specific activity in skeletal muscle. CK is highest in bovine skeletal muscle (165 U/mg) and heart (80 U/mg) and lowest in lung (2 U/mg). Urinary bladder and small intestine have 35-39 U/mg; abomasum, brain and spleen have 20-29 U/mg. Kidney, liver and rumen have <20 U/mg. CK is critical to muscle energy production. CK makes adenosine triphosphate (ATP) available for muscle contraction by catalyzing the transfer of a high-energy phosphate bond from creatine phosphate to adenosine diphosphate (ADP). CK also catalyzes the reverse reaction when muscles are at rest. The muscle contains 8 times more creatine phosphate than ATP thereby providing a reservoir of high-energy phosphate bonds for contraction. Creatine phosphate is the major storage form of high-energy phosphate required by muscle. CK functions in making ATP available for contraction of muscle by phosphorylation of ADP from creatine phosphate (Galitzer S J and Oehme F W, Creatine kinase isoenzymes in bovine tissue, AJVR 46 7:1427-1429, 1985).

The inflammatory myopathies are a group of acquired diseases characterized by an inflammatory infiltrate of the skeletal muscle. The 3 main diseases are dermatomyositis, polymyositis and inclusion body myositis. Patients exhibit markedly elevated levels of CK and lactate dehydrogenase levels consistent with muscle injury. Myositis can be associated with inflammatory bowel disease, coeliac disease and interferon treatment for hepatitis C. Dysphagia to solids and liquids occurs in patients with myositis. The pharyngo-oesophageal muscle tone is lost and therefore patients develop nasal speech, hoarseness, nasal regurgitation and aspiration pneumonia. There is tongue weakness, flaccid vocal cords, poor palatal motion and pooling of secretions in the distended hypopharynx. Proximal esophageal skeletal muscle dysfunction is demonstrated by manometry with low amplitude/absent pharyngeal contractions and decreased upper esophageal sphincter pressures. Corticosteroids and other immunosuppressive drugs comprise the mainstay of treatment. Inclusion body myositis responds poorly to these agents and therefore a myotomy is usually indicated. In summary, myositis mainly involves the skeletal muscles in the upper esophagus with dysphagia, along with proximal muscle weakness (Ebert EC, Review Article: the gastrointestinal complication of myositis, Aliment Pharmacol Ther 31 3:359-365, 2010).

A study was conducted to assess leukocyte chemotactic cytokine and leukocyte subset responses during ultra-marathon running Leukocyte chemokines such as interleukin (IL)-8, interferon gamma-induced protein-10 (IP-10), regulated upon activation, normal T-cell expressed and secreted (RANTES), and eotaxin are involved in leukocyte recruitment. Among 60 male amateur endurance runner volunteers, 18 finished the course (a 308 km continuous race from Kanghwado to Kangneung, South Korea). Blood samples were collected at 0, 100, 200, and 308 km during the race for analysis of white blood cells and serum concentrations of IL-8, IP-10, RANTES, eotaxin, IL-6, CK, and C-reactive protein (CRP). Muscle and liver damage indicators (IL-6, CK, and CRP) were maximally elevated as a result of marathon running Total leukocytes, neutrophils, and monocytes increased significantly during the event (leukocytosis, neutrophilia, and monocytosis, respectively). However, lymphocytes and eosinophils decreased significantly during the event (lymphopenia and eosinopenia, respectively). Serum levels of the neutrophil chemokine IL-8 increased maximally at 100 km and were maintained. Monocyte-lymphocyte chemokine IP-10 concentration decreased during the latter part of the race. The eosinophil chemokine eotaxin decreased gradually during the race. Prolonged endurance ultra-marathon running was associated with significant systemic inflammation and perturbation in leukocyte subsets (Shin Y O Lee J B Leukocyte chemotactic cytokine and leukocyte subset responses during ultra-marathon running Cytokine (2013 February) 61(2):364-9).

CK is also elevated in humans with Severe Acute Respiratory Syndrome (SARS), Duchene muscular dystrophy, cardiomyopathy and febrile seizures in influenza (publications not shown).

CK is elevated in cattle injured by shipment, in cattle bruised in a hydraulic chute or in bull fights or in bull riding in a rodeo. An intramuscular injection can cause an elevated CK (publications not shown).

IFN alpha has been implicated in the pathogenesis of juvenile dermatomyositis (DM). Thirty-nine children with definite/probable juvenile DM were included in a study. Serum samples were obtained at the time of diagnosis from 18 untreated patients with juvenile DM. Second samples from 11 of these patients were obtained at 24 months, while they were receiving treatment, and third samples were obtained from 7 of these patients at 36 months. The remaining 21 children were studied 36 months after their initial diagnosis. Serum IFNalpha activity was measured using a functional reporter cell assay. Patients with juvenile DM had higher serum IFN alpha activity than both pediatric and adult healthy control subjects. In untreated patients, serum IFN alpha activity was positively correlated with serum muscle enzyme levels ($P<0.05$) for CK, aspartate aminotransferase, and aldolase and inversely correlated with the duration of untreated disease ($P=0.017$). At 36 months, serum IFN alpha levels were inversely correlated with muscle enzyme levels in those patients still requiring therapy and with the skin Disease Activity Score in those patients who had completed therapy ($P=0.002$). The authors concluded that serum IFN alpha activity was associated with higher serum levels of muscle-derived enzymes and a shorter duration of untreated disease in patients with newly diagnosed juvenile DM and was inversely correlated with measures of chronic disease activity at 36 months after diagnosis. These data suggest that IFN alpha could play a role in disease initiation in juvenile DM (Niewold T B et al, Elevated serum interferon-alpha activity in juvenile dermatomyositis: associations with disease activity at diagnosis and after thirty-six months of therapy. Arthritis Rheum (2009 June) 60(6):1815-24). There is nothing in this publication that constitutes prior art; instead this publication indicates that IFN may cause or contribute to disease.

Treatment of chicken myoblast cultures with 2-200 IU/ml of interferon (IFN) increased activities of creatine kinase in a dose-dependent in 4- or 6-day cultured muscle cells. (Tomita T and Hasegawa S. Multiple effects of interferon on myogenesis in chicken myoblast cultures. Biochim Biophys Acta 804 3:370-376, 1984).

Murine myoblast cultures treated with 20-20,000 IU of murine IFN/ml medium for 5 days exhibited dose dependent inhibition of CK activity. (Multhauf C and Lough J. Interferon-mediated inhibition of differentiation in a murine myoblast cell line. J Cell Physiol 126 2:211-215, 1986). This publication on the dose dependent effect of IFN on inhibition of CK in myoblast cultures does NOT constitute prior art for the observation in calves discussed below because the dose effect from ORAL IFN could not be predicted from the work on murine myoblast cultures. The dose in murine culture was 20-20,000 IU of IFN/ml of medium while the dose in calves was 8 million times less at 50-800 units per calf or 5 units per KG body weight in the highest oral dose tested. When Tomita and Hasegawa gave 2-200 IU of IFN to chicken myoblast cultures they reported a dose-dependent INCREASE in CK activity.

FIG. 1 illustrates a table 100 describing the effects of orally administered interferon. In one embodiment, said table 100 can comprise a three different variations and effects of orally administered interferon. In one embodiment, said variations can comprise an unweighted least squares linear regression of ck predictor 102, a comparison of regression lines for ck=time 104 and Bartlett's test of equal variances 106. In one embodiment, said unweighted least squares linear regression of ck predictor 102 can comprise a variables 108, a coefficient 110, a std error 112, a student's t 114 and a p 116. In one embodiment, said variables 108 can comprise a constant 118 and a time 120, a r-squared 122, a resid. mean square (MSE) 124, an adjusted r-squared 126 and a standard deviation 128. In one embodiment, said unweighted least squares linear regression of ck predictor 102 can comprise a df 130, a ss 132, a ms, 134, a f 136 and a p 138. In one embodiment, said variables 108 can comprise a regression 140, a residual 142 and a total 144. In one embodiment, said unweighted least squares linear regression of ck predictor 102 can comprise a cases included 146 and a missing cases 148. In one embodiment, said comparison of regression lines for ck=time 104 can comprise a trt 150, a n 152, a intercept 154, a slope 156 and a mse 158. In one embodiment, said trt can comprise a a 160, a b, 162, a c 164 and a d 166. In one embodiment, said Bartlett's test of equal variances 106 can comprise a chi-sq 168, a df 170 and a p 172. In one embodiment, said Bartlett's test of equal variances 106 can comprise a comparison 174, a f 176, a df, 178 and a p 180. In one embodiment, said comparison 174 can comprise a comparison of slopes 182 and a comparison of elevations 184.

FIG. 2 illustrates a graph 200 describing the effects of creatine kinase over a period of time. In one embodiment, said graph 200 can comprise an x-axis representing time 202 (represented in hours) and a y-axis representing creatine kinase in micrograms/ml 204. In one embodiment, said graph can comprise a TRT A 206, a TRT B 208, a TRT C 210, a TRT D 212, a linear (TRT A) 214, a linear (TRT B) 216, linear (TRT C) 218 and linear (TRT D) 220.

In describing and claiming the disclosure, the following terminology will be used in accordance with the definitions set forth below.

As used herein, the term "treating" includes prophylaxis of a specific disease or condition, preventing transmission of the disease to others, delaying onset or progression of the disease, or alleviating the symptoms associated with a specific disease or condition and/or preventing or eliminating said symptoms. In the specific case of a muscle injury or disease, treating includes inhibiting or preventing the release of CK from muscle and or preventing injury as measured by release of CK.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents and includes agents approved by a regulatory agency of the US Federal government or listed in the US Pharmacopeia for use in animals, including humans.

The term "carrier" refers to a diluent, adjuvant, excipient or vehicle with which an active agent is administered.

As used herein, "effective amount" means an amount sufficient to produce a selected effect. For example, an effective amount of interferon is an amount effective to either stabilize a muscle and help prevent the release of CK.

As used herein, "osmolyte" refers to an agent that lends osmolality to the buffered solution or affects hydration or surface tension. Examples include polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, betaalanine, proline, taurine, betaine, octopine, glutamate, sarcosine, y-aminobutyric acid, and trimethylamine N-oxide (TMAO), as described more fully in Yancey et al., Science, 217:1214-1222 (1982) and Schein, Bio/Technology, 8: 308-315 (1990).

Turning now from definitions to embodiments, as disclosed herein compositions and methods are provided to treat animals, including humans, suffering from muscle injury or disease, including for example inflammatory myopathies.

The administration of type I and type III interferons can prevent escape of CK from muscle and can limit the damage to muscle. Bovine interferon, given orally in low dosage, resulted in less CK in the blood of animals given interferon compared to placebo-treated control animals.

In accordance with one embodiment a method of treating a patient suffering from an inflammatory myopathy, including for example dermatomyositis, polymyositis or inclusion body myositis. In one embodiment the method comprises the steps of identifying a patient suffering from muscle injury or disease, including for example, in animals, shipping and handling injury; and administering an amount of a composition comprising a low dose types I and III interferon effective to treat the muscle injury or disease.

In one embodiment the method includes administering a composition comprising an effective amount of type I interferon and a pharmaceutically acceptable carrier. In one embodiment the type I interferon is interferon-alpha or interferon-omega. The interferon containing composition can be administered to the patient through a number of routes, such as orally, intranasally, inhalation, intramuscularly, or intravenously.

In accordance with one embodiment the interferon is administered orally or intranasally. The interferon containing composition can be administered in a single dose, or in several doses/day.

In one embodiment, wherein the interferon containing composition is administered orally, the composition is administered in a form or manner that optimizes contact of the composition with the oral and oral pharyngeal mucosa of the animal or human. In one embodiment the interferon containing composition is prepared as a lozenge, a powder, a liquid form, a dry form, or chewable composition. In accordance with one embodiment the interferon is administered in a form of orally dissolving lozenges.

In one embodiment when the interferon compositions are administered to a ruminant species, the compositions are formulated to bypass the rumen to reach a more favorable digestive environment. Successful bypass of the rumen by an interferon comprising composition can be accomplished using standard microencapsulation technologies known to those skilled in the art. Briefly, the physical methods of encapsulation include spray drying, spray chilling, rotary disk atomization, fluid bed coating, stationary nozzle coextrusion, centrifugal head coextrusion, submerged nozzle coextrusion and pan coating. The chemical methods of encapsulation include phase separation, solvent evaporation, solvent extraction, interfacial polymerization, simple and complex coacervation, in-situ polymerization, liposome technology, and nanoencapsulation. In accordance with one embodiment the active agents (i.e. the interferon composition) are enclosed in an encapsulation system, wherein the encapsulated material has the optimal size and density to move through the rumen of the ruminant before the encapsulating system releases substantial amounts of the active agents. In one embodiment the encapsulated composition provides a controlled, sustained, delayed targeted enteric release of the interferon containing composition. In accordance with one embodiment a method of stabilizing PrPc protein present in a vertebrate species is provided. The method comprises identifying a vertebrate species in need of muscle protection, and administering to such a vertebrate species a composition comprising interferon. In one embodiment the interferon is interferon-alpha that is administered orally in a dosage amount of about 0.01 IU/lb to about 100 IU/lb of animal body weight. The administration of the composition is anticipated to have a prophylactic effect in preventing Muscle injury and also is anticipated to have use in treating individual animals that have already been injured prior to treatment. In accordance with one embodiment the interferon containing composition further comprises trehalose and a disaccharide selected from the group consisting of maltose, lactose and fructose. In one embodiment the disaccharide is anhydrous crystalline maltose.

FIG. 1 illustrates a data table 100. FIG. 2 illustrates a graph 200. An example of the claimed subject matter of this disclosure are set out in said data table 100 and said graph 200. In one embodiment, said data table 100 and said graph 200 can comprise output from a study. In said study, interferon was administered orally to calves and blood samples were taken before and after administration of bovine interferon-alpha, interferon-omega and interferon-lambda to determine what blood components were affected by the oral administration of interferon.

In one embodiment, said data table 100 and said graph 200 provide information on the change in CK before and after administration of interferon orally. Referring to said graph 200, as expected, there was no significant difference in CK mean value between the groups at the first sampling time (0 hour). However, when the calves returned 8 hours later for a second trip through the hydraulic chute, the CK was significantly higher in the placebo-treated calves (group A). The CK was significantly lower (P=0.04) in the high dose interferon (IFN) group (Group D). The CK was significantly lower (P=0.06) in the middle dose IFN group (Group C). The CK was significantly lower (P=0.13) in the low dose IFN group (Group B). This observation occurred with only 4 calves per treatment group after only a single oral dose of IFN.

A second dose of IFN was given at 8 hours. The calves returned for a third trip through the hydraulic chute at 24 hours (16 hours after the second dose of IFN). At 24 hours, the CK was significantly lower (P=0.12) in the middle and high dose IFN groups (Groups C & D). The CK was significantly lower (P=0.19) in the low dose IFN group (Group B).

Serum CK activity increases rapidly after muscle injury and decreases rapidly after the injury ceases. The half-life of CK in cattle is reported to be 4 hours. In the present study, the increase in serum CK was probably attributed to muscle injury in the hydraulic chute and from the needle stick to collect blood. The mean CK was higher at 8 hours after sampling than it was at 24 hours (16 hours after sampling) probably because half-life decline after the acute injury.

Accordingly, the oral administration of low dose interferon-alphaomega and -lambda resulted in less CK in the blood 8 hours after a single oral dose of interferon and 16 hours after a second dose of interferon reflecting less muscle injury or disease, and is anticipated to be efficacious in treating muscle injury or disease.

FIG. 3 illustrates a flow chart illustrating a method of treating muscle injury or disease comprising of a first step 302, a second step 304, a third step 306, and a fourth step 308. In one embodiment, said first step 302 comprises identifying a humans or an animals at risk. In one embodiment, said second step 304 comprises administering to said humans or said animals a composition comprising a dose of an interferon. In one embodiment, said third step 306 comprises orally administering said interferon to said humans or said animals. In one embodiment, said fourth step 308 comprises dosing said interferon at about 0.01 IU/lb to about 100 IU/lb of a body weight of said humans or said animals.

FIG. 4 illustrates a flow chart illustrating a method of stabilizing muscle in a vertebrate species comprising of a first step 402, and a second step 404. In one embodiment, said first step 402 comprises administering a composition to a vertebrate species. In one embodiment, said second step 404 comprises orally administering said interferon in a dosage amount of about 0.01 IU/lb to about 100 IU/lb of an animal body weight.

FIG. 5 illustrates a flow chart illustrating a method of stabilizing muscle in a vertebrate species comprising of a first step 502, and a second step 504. In one embodiment, said first step 502 comprises administering a composition to a vertebrate species. In one embodiment, said second step 504 comprises orally administering said composition in a liquid form.

FIG. 6 illustrates a flow chart illustrating a method of stabilizing muscle in a vertebrate species comprising of a first step 602, and a second step 604. In one embodiment, said first step 602 comprises administering a composition to a vertebrate species. In one embodiment, said second step 604 comprises administering said composition as a feed supplement in a dry form admixed with an animal feed formulation.

In one embodiment, a supplemented animal feed can comprise said feed supplement admixed with said animal feed formulation. In one embodiment, said animal feed formulation is for a ruminant species. In one embodiment, said feed supplement is prepared in an encapsulated form. In one embodiment, said encapsulated form of said feed supplement bypasses said rumen before releasing a contents of said feed supplement to said digestive tract of said ruminant species.

FIG. 7 illustrates a flow chart illustrating method of treating muscle injury or disease comprising of a first step 702, and a second step 704. In one embodiment, said first step 702 comprises administering a composition comprising interferon-alpha, interferon-omega and/or interferon-lambda. In one embodiment, said second step 704 comprises dosing said interferon in a dosage amount of about 0.01 IU/lb to about 100 IU/lb of animal body weight.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A method of limiting the release of Creatine Kinase (CK) in a ruminant species with muscle injury caused in and after being in a hydraulic chute, comprising:
    identifying a ruminant species suffering from or likely to sustain a muscle injury in the following 24 hours after being in a hydraulic chute;
    administering an interferon containing composition, comprising an interferon-alpha, to said ruminant species to limit the release of CK from a muscle of said ruminant species during and after said muscle injury; wherein said interferon-alpha is orally administered to said ruminant species within 8 hours of said muscle injury in a dosage amount of about 0.01 IU/lb to about 100 IU/lb of an animal body weight of said ruminant species.

2. The method of claim 1 further comprising:
    including a trehalose and a disaccharide in said interferon containing composition of an interferon-alpha; wherein said disaccharide is selected from a group consisting of
        a maltose,
        a lactose and
        a fructose.

3. The method of claim 2 wherein
    said disaccharide is an anhydrous crystalline maltose.

4. The method of claim 1 further comprising:
    orally administering said interferon containing composition in a liquid form.

5. The method of claim 1 further comprising:
    administering said interferon containing composition in a dry form admixed with an animal feed formulation.

6. The method of claim 1 further comprising:
    said interferon containing composition is formulated to bypass the rumen to reach a more favorable digestive environment by using standard microencapsulation technologies selected among spray drying, spray chilling, rotary disk atomization, fluid bed coating, stationary nozzle coextrusion, centrifugal head coextrusion, submerged nozzle coextrusion and pan coating.

7. The method of claim 1 further comprising:
    administering said interferon containing composition one or more times a day.

8. The method of claim 1 further comprising:
    optimizing contact of said interferon containing composition with the oral and oral pharyngeal mucosa of said ruminant species.

9. The method of claim 1 further comprising:
    administering said interferon containing composition at least twice within 8 hours of a muscle injury to said ruminant species.

10. The method of claim 1 further comprising:
    said interferon containing composition comprises said interferon-alpha and a pharmaceutically acceptable carrier; and
    said pharmaceutically acceptable carrier comprises one or more among a phosphate buffered saline solution, a water and an emulsion such as an oil/water or water/oil emulsion, and various types of wetting agents.

11. The method of claim 1 further comprising:
    said ruminant species comprises one or more chosen among bovine, horses, calves, and pigs.

12. The method of claim 1 further comprising:
    said ruminant species comprise calves.

* * * * *